US009792729B2

(12) United States Patent
Kaufman et al.

(10) Patent No.: US 9,792,729 B2
(45) Date of Patent: Oct. 17, 2017

(54) SYSTEM AND METHOD FOR CONTEXT PRESERVING MAPS OF TUBULAR STRUCTURES

(71) Applicant: THE RESEARCH FOUNDATION OF STATE UNIVERSITY OF NEW YORK, Stony Brook, NY (US)

(72) Inventors: Arie Kaufman, Plainview, NY (US); Xianfeng David Gu, Plainview, NY (US); Joseph Marino, Port Jefferson Station, NY (US); Wei Zeng, Stony Brook, NY (US)

(73) Assignee: THE RESEARCH FOUNDATION FOR THE STATE UNIVERSITY OF NEW YORK, New York, NY (US)

( * ) Notice: Subject to any disclaimer, the term of this patent is extended or adjusted under 35 U.S.C. 154(b) by 680 days.

(21) Appl. No.: 14/353,168

(22) PCT Filed: Oct. 22, 2012

(86) PCT No.: PCT/US2012/061356
§ 371 (c)(1),
(2) Date: Apr. 21, 2014

(87) PCT Pub. No.: WO2013/059807
PCT Pub. Date: Apr. 25, 2013

(65) Prior Publication Data
US 2014/0362080 A1    Dec. 11, 2014

Related U.S. Application Data

(63) Continuation of application No. 61/549,916, filed on Oct. 21, 2011.

(51) Int. Cl.
*G06T 19/00*    (2011.01)
*G06T 15/00*    (2011.01)
*A61B 34/10*    (2016.01)

(52) U.S. Cl.
CPC .......... *G06T 19/003* (2013.01); *G06T 15/005* (2013.01); *G06T 19/00* (2013.01);
(Continued)

(58) Field of Classification Search
CPC ..... G06T 19/003; G06T 15/005; G06T 19/00; G06T 2219/008; G06T 2219/021; A61B 2034/105
See application file for complete search history.

(56) References Cited

U.S. PATENT DOCUMENTS

2008/0018646 A1* 1/2008 Farag .................. G06T 7/604
345/424
2009/0225077 A1* 9/2009 Sudarsky ............. G06T 7/0085
345/423

(Continued)

FOREIGN PATENT DOCUMENTS

EP         1892668          2/2008
WO    WO 2010/036716      1/2010
WO    WO 2011110867 A1 *  9/2011  .......... G06T 7/0024

OTHER PUBLICATIONS

NPL, Qiu et al., Colon flattening with discrete Ricci flow, MICCAI workshop, 2008.*

(Continued)

*Primary Examiner* — Stephen R Koziol
*Assistant Examiner* — Pinalben Patel
(74) *Attorney, Agent, or Firm* — Andrews Kurth Kenyon LLP

(57) ABSTRACT

A computer-based method for generating a context preserving mapping of tubular structures represented by a 3D dataset having the steps of projecting a skeleton of a 3D tubular structure on to a 2D plane, and adjusting the projected skeleton to correct projection imbued distortion in skeleton length. The 2D projected skeleton is processed to remove intersections, and a surface boundary around the 2D skeleton is determined for the map. The 3D surface of the skeleton is mapped to match the 3D boundary to create a 3D map of the tubular structure.

33 Claims, 12 Drawing Sheets

(52) U.S. Cl.
CPC ... *A61B 2034/105* (2016.02); *G06T 2219/008* (2013.01); *G06T 2219/021* (2013.01)

(56) References Cited

U.S. PATENT DOCUMENTS

2010/0079455 A1* 4/2010 Wei .................... A61B 5/02007
                                                                345/424
2010/0215226 A1* 8/2010 Kaufman .............. G06K 9/342
                                                                382/128

OTHER PUBLICATIONS

NPL, Christoph Spuhler et al.: Fast and robust extraction of centerlines in 3D tubular structures using a scattered-snakelet approach, Medical Imaging. International Society for Optics and Photonics, 2006.*

Dave, Sanjay B., et al. "Straightening the colon with curved cross sections: an approach to CT colonography." Academic Radiology 6.7 (1999): 398-410.*

Zhang, Zhan, et al. "Fast algorithm for soft straightening of the colon." Academic radiology 7.3 (2000): 142-148.*

International Search Report for International Patent Application No. PCT/US2012/061356 mailed on Jan. 24, 2013.

Written Opinion for International Patent Application No. PCT/US2012/061356 mailed on Jan. 24, 2013.

* cited by examiner

Abutment

Loop

Crossing

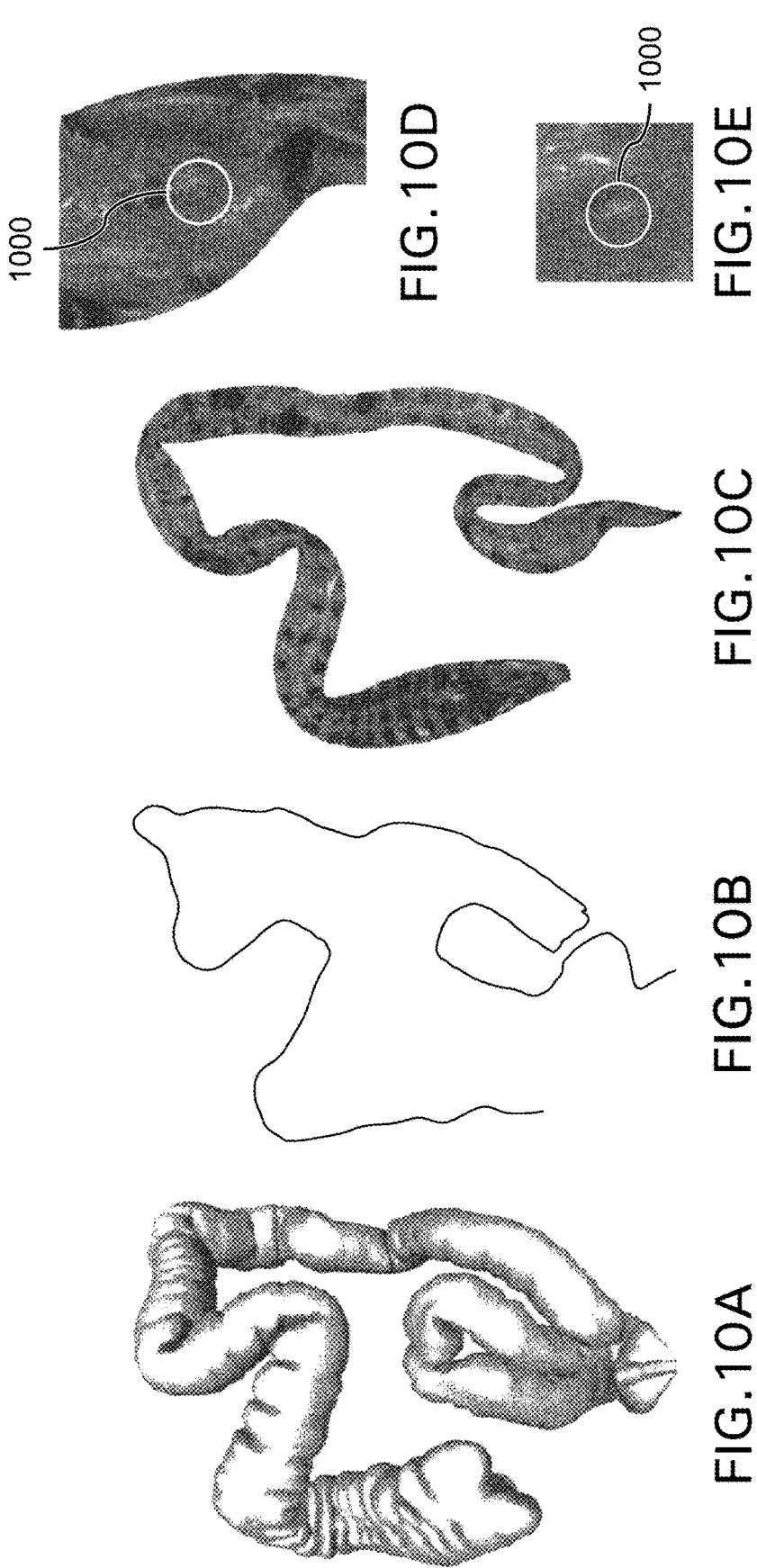

SYSTEM AND METHOD FOR CONTEXT PRESERVING MAPS OF TUBULAR STRUCTURES

CROSS-REFERENCE TO RELATED APPLICATIONS

The present application relates to and claims the benefit and priority from International Patent Application No. PCT/US2012/061356 filed on Oct. 22, 2012, pursuant to 35 U.S.C. §119(e) from U.S. Provisional Patent Application Ser. No. 61/549,916 filed on Oct. 21, 2011, the entire disclosures of which are hereby incorporated herein by reference.

STATEMENT OF GOVERNMENT RIGHTS

This invention was made with government support under grant number R01EB7530 awarded by the National Institute of Health and grant numbers IIS0916235, CCF0702699 and CNS0959979 awarded by the National Science Foundation. The government has certain rights in the invention.

FIELD OF THE DISCLOSURE

The present disclosure relates generally to the visualization and navigation of a 3D tubular structure, and more specifically, relates to a 2D representation of a 3D tubular structure through the use of a skeleton representation that preserves the geometric context of the 3D structure in the 2D flattened representation.

BACKGROUND INFORMATION

A common application in computer visualization is to virtually navigate inside a tubular structure in order to inspect its walls, such as in a virtual colonoscopy. In providing such navigation, it can be desirable to maintain an external view of the object such that one's position within the structure can be easily determined. This can be important when the structure being examined can look similar at different regions. However, using a typical 3D model for this purpose can lead to many problems. For instance, for a complex curving structure such as a colon, sections can occlude each other when they exist in the same region on the viewing plane and at different depths along the view direction. Such problems can necessitate rotation of the 3D structure.

Extracting a skeleton curve of an object is a popular method of compactly representing the general geometric shape of a structure. Significant work has been done to develop methods of extracting these skeleton curves. For example, skeleton extraction from volumetric medical data by connecting centerlines based on a medial voxel path is previously known using a distance from a boundary field with penalty weights to obtain general skeletons of treelike structures. Obtaining a skeleton directly from a mesh by contracting the surface, without any need for a volumetric representation, is also known. In addition, both surface and curve skeletons from genus zero structures have been extracted through the use of advection to move mass from the object's surface to its skeleton. The use of least squares optimization has been suggested for extracting curve skeletons in an efficient manner which can be insensitive to noise. It is also known that curve skeletons can be approximated for data from incomplete point clouds based on a generalized rotational symmetry axis for a set of points.

There are many uses for skeleton curves in the fields of computer graphics and visualization, and their 1D representation of 3D objects is useful for compact shape descriptions, navigation, animation, and analysis. Skeleton curves can be used to drive shape deformations. They have also been used in describing shape to allow for the creation of shape-based transfer functions. They can commonly be used for navigation in endoscopic visualizations, such as a virtual colonoscopy, where accurate curves can be important during the navigation.

A flattened representation of a structure can be useful for providing an overview of the entire structure in a single 2D view. Common methods of creating flattened representations straighten the object such that it can be difficult to locate where a position would correspond to in the actual tubular structure by simply looking at the flattened representation. This is evident, for example, in the case of flattening a virtual colon wall to a long linear strip. Though the 3D colon structure is often classified into separate sections based on the major bends it contains, this information can be lost in the flattened and straightened representation.

Thus, it may be beneficial to provide a 2D representation of a 3D tubular structure through the use of a skeleton representation that preserves the geometric context of the 3D structure in the 2D flattened representation such that the 2D flattened representation can be used to guide navigation within the structure, does not contain intersections which would cause occlusions, and overcomes at least some of the problems described above.

SUMMARY OF EXEMPLARY EMBODIMENTS

These and other deficiencies can be addressed with the exemplary embodiments systems, methods, and computer readable storage media for 2D contextual mapping of a 3D tubular structure set forth in the present disclosure.

A skeleton curve, also called the centerline, through the tubular structure can be first discretized, using, for example, a spacing of 1 mm along the skeleton. An orthogonal projection of this discretized skeleton can then be performed to project the points on a 2D plane. This can be accomplished using a known preferred viewpoint, such as the case with the colon, or to a plane which minimizes structural overlap. A lengthening procedure can then be performed to account for shrinkage in distance due to portions of the skeleton which are orthogonal to the projection plane. A straightened version of the skeleton can be created with equal spacing, and can be bent based on the angles in the projected skeleton. The resulting lengthened projected skeleton can be untangled to remove intersections. The skeleton can then be adjusted based on the radius along the skeleton such that there is room to accommodate the flattened surface without overlap.

To prepare the mesh for mapping, the 3D representation of the tubular structure can be first virtually sliced open and flattened from one end to other to create a boundary. A correspondence can then be found between each boundary vertex and the skeleton. The radius for each skeleton point can then be associated with the corresponding boundary vertices. These boundary vertices can be embedded into the 2D domain at their associated radius, orthogonal to the 2D skeleton. The end result can be a placement of the boundary of the mesh in 2D, which can contain the result of the mapping from the 3D structure to the 2D map.

The exemplary system, method, and computer readable medium can then map the surface of the structure to a 2D map through the use of a Ricci flow, or the like, to map the original surface to a 2D rectangle. The boundary placement in 2D can be triangulated also using a Ricci flow to map this surface to a 2D rectangle. A correspondence can be found between these two rectangles by minimizing the harmonic energy. This allows the original 3D surface to be mapped to the target boundary. To display the surface, surface rendering h normal information appropriated from the 3D surface can be used. Alternatively, volumetric ray casting through the original CT data from which the mesh is extracted can be utilized to generate more detailed images.

Exemplary embodiments of the present disclosure include exemplary systems, methods, and computer readable mediums for generating context preserving maps of tubular structures represented by a 3D dataset, the exemplary system, method, and computer readable medium includes projecting a skeleton of a 3D tubular structure on to a 2D plane, adjusting the projected skeleton to correct projection imbued distortion in skeleton length, processing the skeleton to remove intersections, determining a boundary for the map, and mapping a 3D surface of the skeleton to match the 3D boundary to create a 3D map.

In certain embodiments, the skeleton is modified to separate areas lying close to each other. In some embodiments, volumetric rays are cast through an original CT data from which a mesh is extracted to generate a more detailed 3D map. In accordance with certain embodiments, a surface of a 2D structure of a 2D map is mapped to a surface of a 2D rectangle. In accordance with certain embodiments, the 2D map is mapped using Ricci flow. In some embodiments, the boundary is determined by slicing open the skeleton from end to end and each boundary is corresponded with a vertex with the skeleton. In some embodiments, each boundary vertex is embedded into 2D at an associated radius orthogonal to the 2D skeleton. In accordance with certain embodiments, the skeleton is processed by untangling the skeleton. In accordance with certain embodiments, the untangling of the skeleton comprises searching for and correcting the skeleton for at least one of abutments, loops or crossings.

In some embodiments, the steps involved in untangling the skeleton can be prioritized. In one example, the priority for searching the skeleton can begin with searching for abutments, then searching for loops, and then searching for crossings. In some embodiments, the projection of the skeleton is based on a discretized skeleton curve. In accordance with certain embodiments, the adjusting of the skeleton can include straightening and/or lengthening the skeleton. In accordance with certain embodiments, lengthening of the skeleton can include bending a straight skeleton with even spacing into a shape of a projected skeleton. In some embodiments, the projecting of the skeleton can include projecting points of an orthogonal projection of a 3D skeleton on to a 2D plane. In some embodiments, the 3D map is viewed on a display.

An advantage of the present disclosure over other surface mapping technologies is that the present mapping preserves the geometric context of the structure.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 10A shows a tubular structure in its original mesh form;

FIG. 10B shows a 2D shaped skeleton of the tubular structure of FIG. 10A;

FIG. 10C shows a 2D rendered result of the flattened colon wall corresponding to the 2D sloped skeleton of FIG. 10B according to an exemplary embodiment of the present disclosure;

FIG. 10D shows a close-up view of a region of the rendered result of FIG. 10C showing a polyp;

FIG. 10E shows a further close-up view of the close-up view of FIG. 10D showing a polyp;

Figure 1:
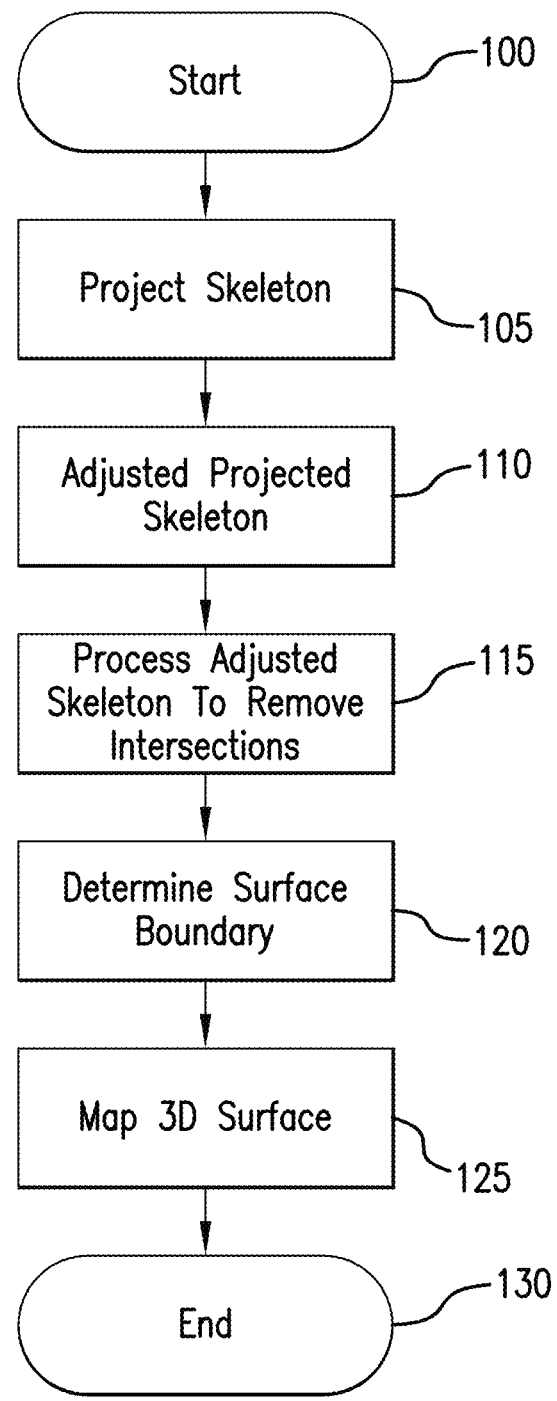
FIG. 1 is a simplified flow diagram that illustrates an exemplary method for performing context preserving mapping of tubular structures according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the Figures, it is done so in connection with the illustrative embodiments and is not limited by the particular embodiments illustrated in the Figures.

DETAILED DESCRIPTION OF THE DISCLOSURE

The exemplary embodiments of the present disclosure may be further understood with reference to the following description and the related appended drawings. The exemplary embodiments of the present disclosure relate to an exemplary system, method and computer readable medium for context preserving mapping of tubular structures. Specifically, the exemplary system, method and computer readable medium creates a 2D representation of a 3D tubular structure allowing the viewer to easily determine the particular 3D location being viewed. The exemplary embodiments are described with reference to a colon, although those having ordinary skill in the art will understand that the exemplary embodiments of the present disclosure may be implemented on any generally tubular structure.

The creation of a context preserving map is based upon manipulating the skeleton of the structure, which can be found using any of the standard methods. FIG. 1 is a simplified flow diagram describing a summary of a method of generating such a context preserving map in accordance with the present systems and methods. Referring to FIG. 1, at step 105, the skeleton of a 3D tubular structure can be projected on to a 2D plane. At step 110, the projected skeleton can be adjusted to correct projection imbued distortion, such as in the skeleton length for portions of the skeleton aligned along the direction of projection. At step 115, the skeleton can be processed to untangle and remove intersections from the 2D projection, such as abutments, loops and crossings. The projection can be spaced properly to prevent self-intersection of the structure's surface. All operations can be performed on a discretized version of the skeleton with initial equal spacing between points. At step 120, a surface boundary around the 2D skeleton can be determined for the map. At step 125, the 3D surface of the skeleton can be mapped to match the 3D boundary in order to create a 3D map. At step 130, the method ends. The resulting 2D skeleton and 3D map effectively preserves the context of the 3D structure.

The original skeleton of the 3D structure can be first projected to a 2D plane, such that all Z values become zero. Since this projection can be used as the basis for a map, perspective distortion is unnecessary, and even detrimental, and thus an orthogonal projection can be used. The projection can be performed using the standard orthogonal projection matrix, for example:

$$\begin{bmatrix} x' \\ y' \end{bmatrix} = \begin{bmatrix} u_x & u_y & u_z \\ v_x & v_y & v_z \end{bmatrix} \begin{bmatrix} x \\ y \\ z \end{bmatrix},$$

where u and v can be the right and up vectors of the projection plane.

Figure 2C:
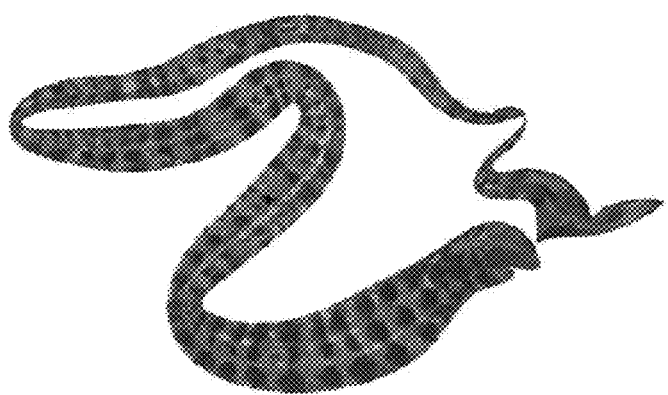
FIG. 2C is a flattened map of the colon surface of the 3D visualization of FIG. 2A.
Figure 2B:
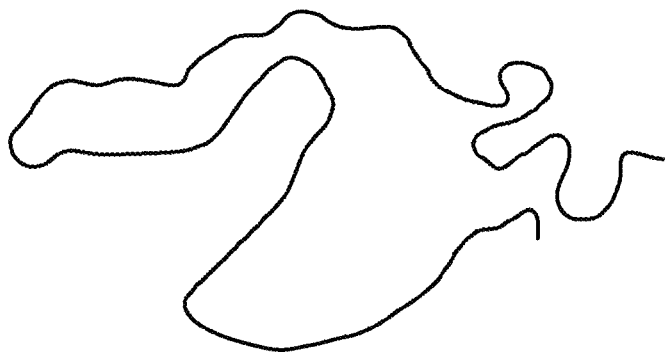
FIG. 2B is a projected 2D skeleton of the 3D map of FIG. 2A that has been corrected in accordance with an exemplary embodiment of the present disclosure.
Figure 2A:
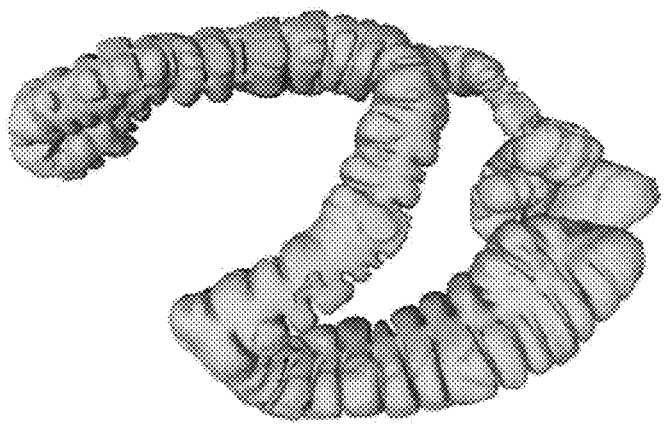
FIG. 2A is a 3D visualization of a tubular structure to be mapped into a 2D representation.
Figure 3D:
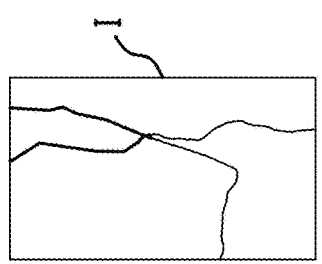
FIG. 3D is a close-up view of intersection region I from FIG. 3B.
Figure 3E:
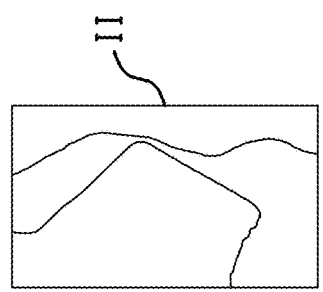
FIG. 3E is a close-up view of intersection region II from FIG. 3C.
Figure 3C:
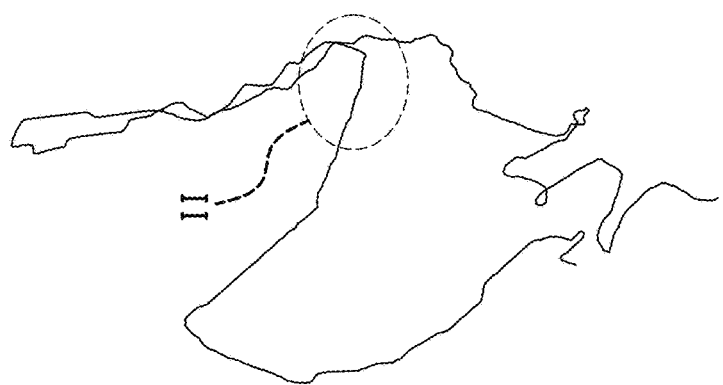
FIG. 3C is a projection of the skeleton of FIG. 3B that has been untangled according to an exemplary embodiment of the present disclosure.
Figure 3B:
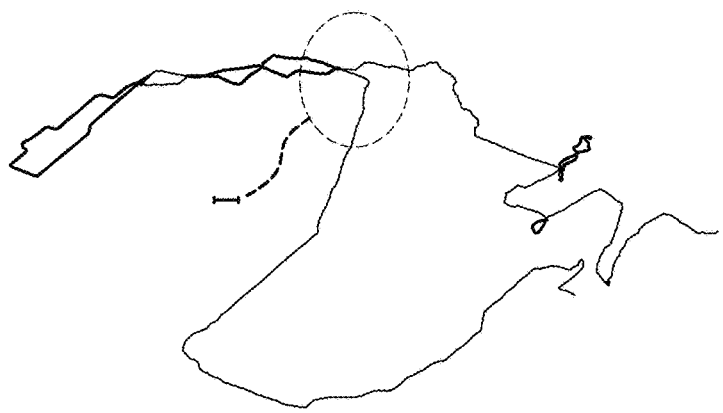
FIG. 3B is a projection of the skeleton of FIG. 3A that has been lengthened according to an exemplary embodiment of the present disclosure.
Figure 3A:
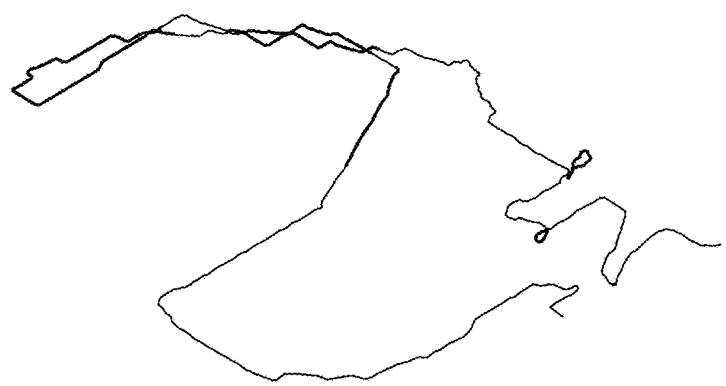
FIG. 3A is a 2D projection of the skeleton of FIG. 2A.

The projection plane can be chosen to be an optimal viewing plane for the structure. For most types of objects, especially in medical applications, a canonical view is known in the art to provide a view that is familiar to the user. If such a view is not known a priori, a plane which minimizes structural overlap and skeletal intersections can be used. A 2D projected skeleton of the colon of FIG. 2A is shown in FIG. 3A.

When performing the orthogonal projection to project the 3D structure on to a 2D plane, the lengths of certain portions of the skeleton can be substantially diminished if the segment direction is aligned with the view direction of the projection plane. The closer to parallel the segment direction and view direction are, the greater the loss of length. To recover this length in the 2D skeleton, a lengthening procedure can be applied that bends a straight skeleton with even spacing into the shape of the projected skeleton.

For every point along the projected skeleton (except endpoints), its two neighboring skeleton points can be used to create two vectors $V_1$ and $V_2$, and the angle between them can be calculated in a standard way based on the law of cosines:

$$\theta = \cos^{-1} \frac{v_1 \cdot v_2}{|v_1||v_2|}. \qquad (2)$$

All of the points in the skeleton can then be set in a straight line, with equal spacing between them equivalent to the original spacing of the 3D discretized skeleton. Starting at the beginning, the corresponding angle θ can be used to rotate points p=(x.y) around the current point $p_0=(x_0, y_0)$ as follows:

$$\begin{bmatrix} x' \\ y' \end{bmatrix} = \begin{bmatrix} \cos\theta & -\sin\theta \\ \sin\theta & \cos\theta \end{bmatrix} \begin{bmatrix} x - x_0 \\ y - y_0 \end{bmatrix} + \begin{bmatrix} x_0 \\ y_0 \end{bmatrix}. \qquad (3)$$

If the original rotation was clockwise instead of counter-clockwise in relation to the normal of the projection plane, then the transpose of the matrix can be used accordingly. This can be performed for all points along the skeleton until the end is reached. After this process, the length of the skeleton from its original 3D shape can be substantially preserved, while the geometric structure of the projected 2D skeleton can also be substantially preserved. The lengthened 2D skeleton of a colon is shown in FIG. 3B.

Figure 5A:
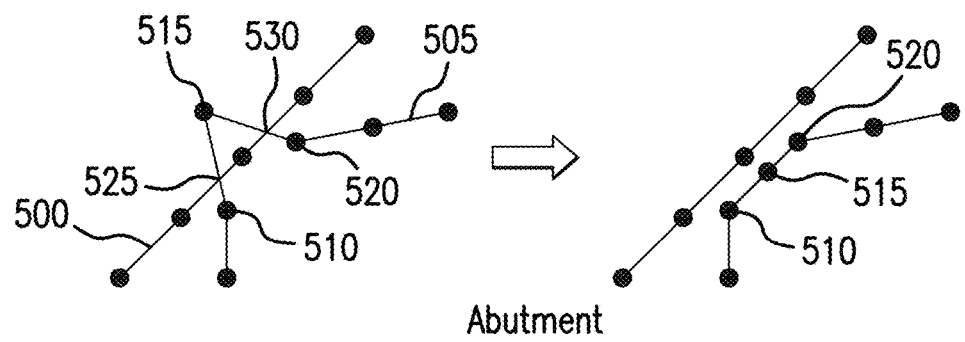
FIG. 5A shows an exemplary abutment intersection that can be corrected in accordance with the present disclosure.
Figure 5B:
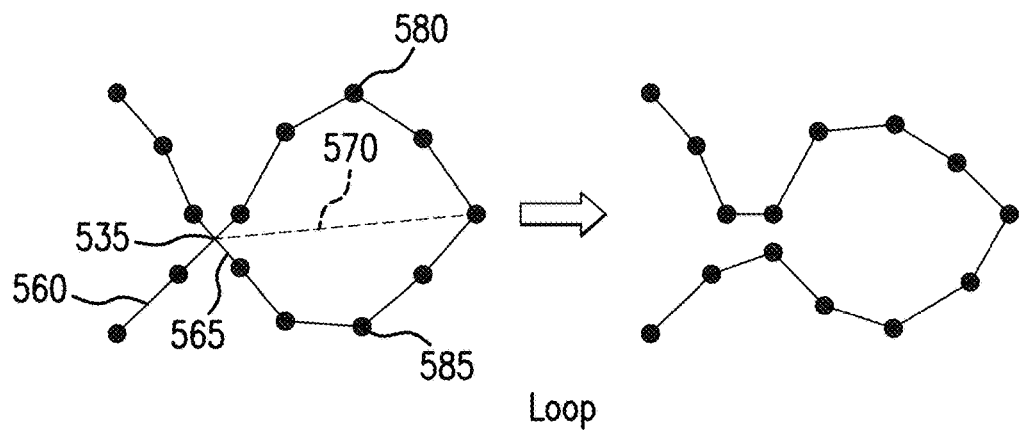
FIG. 5B shows an exemplary loop intersection that can be corrected in accordance with the present disclosure.
Figure 5C:
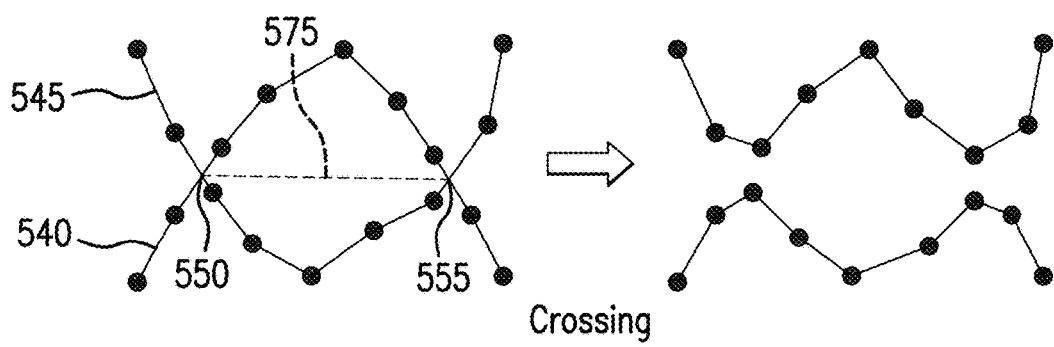
FIG. 5C shows an exemplary crossing intersection that can be corrected in accordance with the present disclosure.

Given the lengthened 2D projected skeleton, the 2D projected skeleton can be untangled such that no intersections are present. This process can maintain the general shape of the structure (see FIGS. 3B-E). This can be done by looking for and removing three types of intersections: loops, crossings, and abutments. An example of each type of intersection and the corresponding result of untangling is shown in FIGS. 5A-C.

Figure 4:
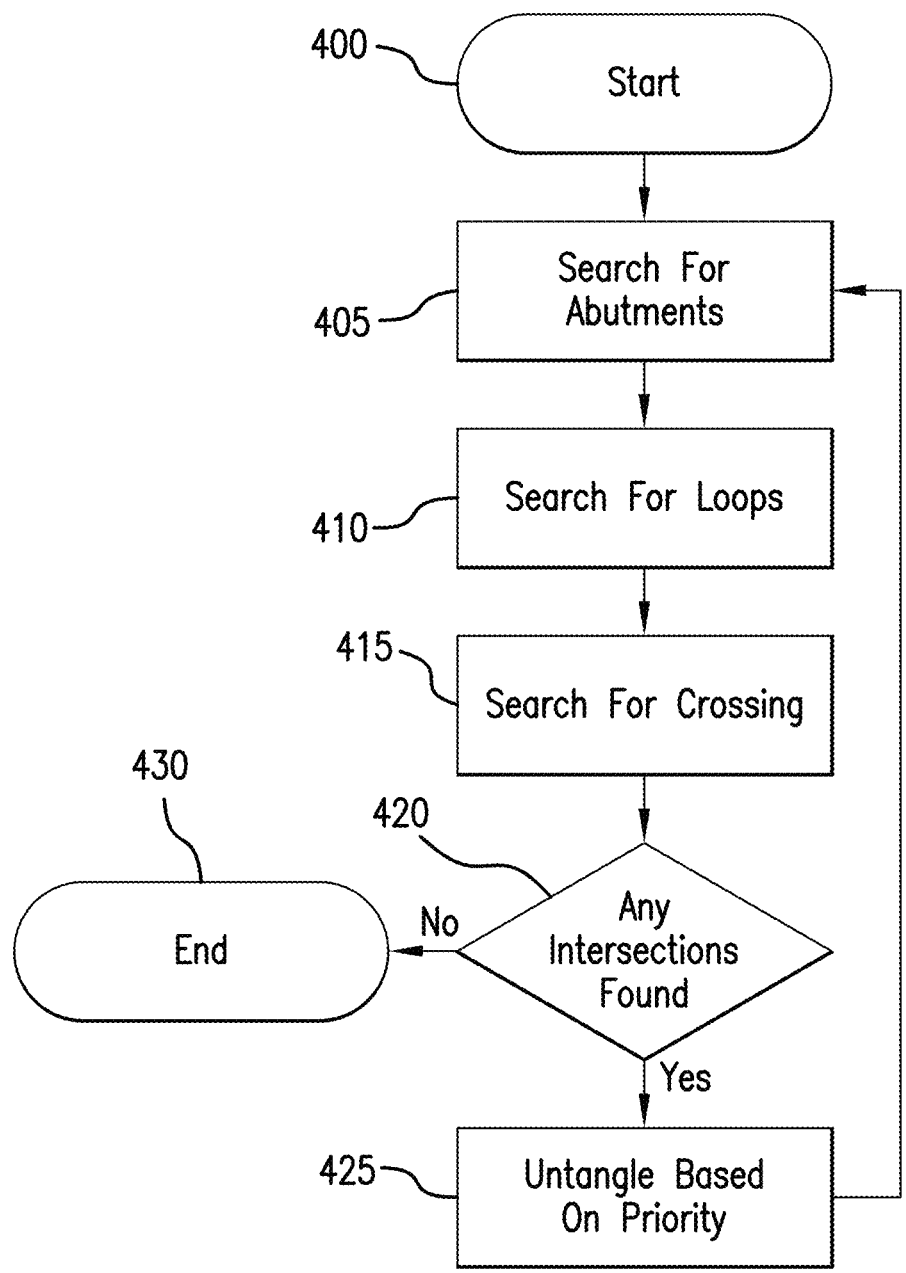
FIG. 4 is a simplified flow diagram that illustrates an exemplary method for untangling a skeleton according to an exemplary embodiment of the present disclosure.

FIG. 4 is a simplified flow chart that illustrates an exemplary method for untangling a skeleton according to an exemplary embodiment of the present disclosure. At step 400, the method begins. At step 405, abutments in the skeleton are searched for and tagged. At step 410, loops in the skeleton are searched for and tagged. At step 415, crossings in the skeleton are searched for and tagged. If no intersections are located at step 420, the method ends at step 430. If any intersections are located at step 420, the intersections can be untangled at step 425 based on a priority, which can be to first untangle abutments, then untangle loops, and finally untangle crossings. The procedure can be repeated until no intersections are found in the 2D skeleton, and the method ends at step 430.

An abutment (see FIG. 5A) occurs when a center point 515 among three consecutive discrete skeleton points (510, 515, 520) of a first segment 505 lies on the opposite side of another line segment 300 of the skeleton than the other two points (510, 520). This causes both line segments formed by the three points to intersect the skeleton at a single line segment 500, and thus contains two points of intersection (525, 530). A loop (see FIG. 5B) occurs when a skeleton comes around and crosses over itself without any other intersections within the formed loop. This creates one intersection point 535. A crossing (see FIG. 5C) occurs when two sections of a skeleton (540, 545) intersect each other without any loops or abutments between them. This contains two intersection points (550, 555).

To remove these intersections, all intersections of the skeleton are first found. Each intersection can be located twice within the list, once for each time it is encountered when tracing the path. The list of intersections can then be searched to locate the three different types listed above. Given that an intersection is made of two intersecting line segments in the discrete case, each intersection can be represented by four points, the first two points representing the endpoints of the first line segment and the second two points representing the endpoints of the second line segment along the skeleton. The points themselves are ordered as their order along the skeleton. Each of the three intersections can be identified as described below:

An abutment, as shown in FIG. 5A, can be located by finding two consecutive intersections (525, 530) for the same line segment 300 (intersecting two separate line segments). A loop, as shown in FIG. 5B, can be located as two consecutive intersections where the pair of line segments for the two intersections is the same. For example, segment 560 intersects segment 565 at point 535. Continuing to traverse the skeleton, the next intersection would be segment 565 intersecting segment 560 at point 535. A crossing can be located as two consecutive intersections (550, 555) that do not meet either of the above two conditions.

After searching the list of intersections, the first intersection of the highest priority that is found can be corrected first. The priority of intersections, in order from high priority to low priority can be an abutment, a loop, and then a crossing. Correction of each type of intersection is described below.

An abutment can be removed by simply setting the offending point 315 to the average of its two neighbor points. This is illustrated in the right hand side of FIG. 5A where point 515 is now moved such that it does not intersect segment 500. A loop can be removed by first creating a line segment 570 from the loop intersection point 535 to the median point of the loop. All points within the loop defined by the ends of lines segment 570 (e.g., 580, 585) can be reflected from one side of the line segment to the other side of the line segment, becoming untangled. A crossing can be removed similarly to a loop. A line segment 575 spanning the two intersection points can be found. All points within the crossing defined by the ends of line segment 575, on both segments of the skeleton, can be reflected to the other side of the line segment 570, becoming untangled.

Since performing one correction can cause new intersections to arise, the skeleton can be searched again after every correction procedure to find all remaining intersections (See FIG. 4). This is repeated until no intersections are found along the skeleton after an untangling operation. After untangling, the skeleton can be iteratively smoothed to remove small sharp features (see FIG. 6A).

Figure 6A:
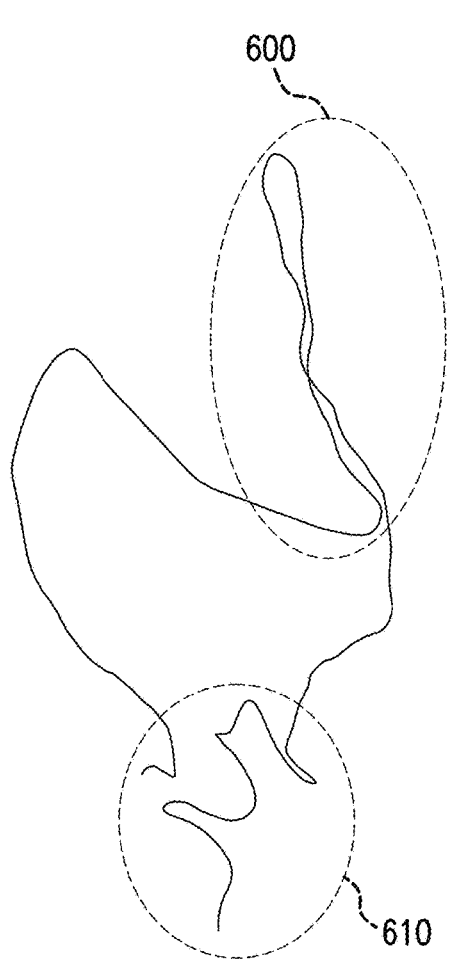
FIG. 6A shows a projection of a smooth version of an untangled 2D skeleton according to an exemplary embodiment of the present disclosure.
Figure 6B:
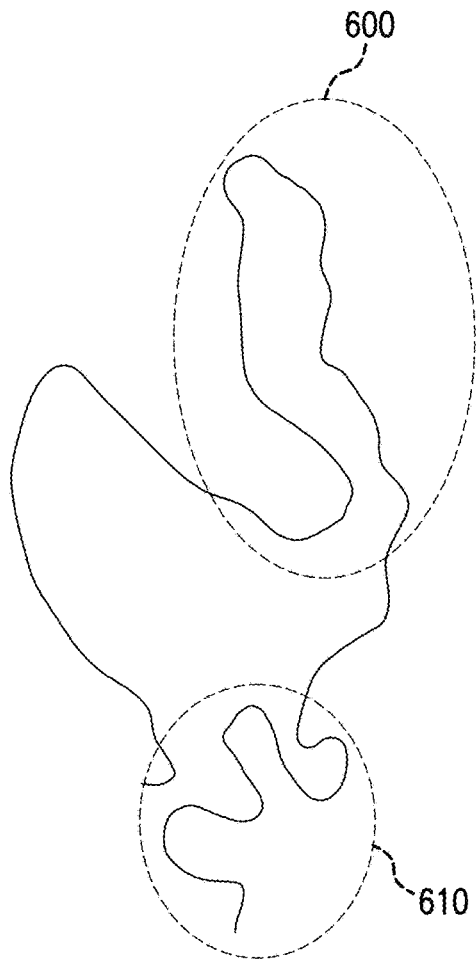
FIG. 6B shows a projection of a spaced and smooth version of an untangled 2D skeleton according to an exemplary embodiment of the present disclosure.

After the untangling procedure, several segments of the skeleton can lie very close to each other due to the orientation of the projection plane as shown in regions 600 and 610 of FIG. 6A. These areas where regions in the skeleton are close can be spaced out so that there is room for the colon surface boundary when flattened without having adjacent segments overlap as shown in corresponding regions 400 and 610 in FIG. 6B. The radius of the structure along the skeleton is recorded, and the 2D skeleton points can be translated perpendicular to their direction such that the radius segment from every point does not intersect other sections of the skeleton. For each offset of the skeleton points, if an intersection is created, the offset can be undone. In this way, no new intersections will occur. Neighboring skeleton points can also be moved slightly to help avoid sharp bends. At the end, iterative smoothing can be applied to the entire skeleton to yield a clean path. (see FIG. 6B).

Given the untangled skeleton path of the 3D structure, the boundary for the flattened surface can be determined and placed in relation to it. In addition to preserving the overall contour of the skeleton of the structure, it is desirable to represent the general size of structure along the skeleton. This can be accomplished calculating the approximate radius along the skeleton and using it to control the layout of the boundary. This can have the effect of condensing the surface perpendicular to the skeleton, but the overall relation of size between regions can still be observed.

In mapping a tubular structure to a plane, it can be beneficial if the structure has a single boundary. The structure can be discretely represented by a closed surface triangular mesh (i.e., without boundaries), which is initially topologically equivalent to the sphere in 1R3 (it has an Euler characteristic number x=2). To make the surface instead topologically equivalent to a plane in L3, it can be sliced open from one end to the other, creating a single boundary. Although this boundary could technically be located anywhere, it is beneficial if it matches the skeleton on the original structure.

To locate the path along which the mesh is to be sliced open, Dijkstra's shortest path algorithm can be used. This algorithm is advantageous for structures with features such as bumps and valleys, through which the cutting line should not pass, as Dijkstra's algorithm naturally tends to avoid these areas and instead locates a path along more uniform regions. In the case of the colon, this means that the slicing path will generally not go through features such as the haustral folds. For Dijkstra's algorithm, the starting point can be taken to be the vertex on the surface mesh nearest to one end of the 3D skeleton. The target point can then be taken as usual as the surface vertex with the greatest distance from the source. Alternatively, the surface vertex located nearest to the other end of the skeleton can be taken as the target.

Figure 7A:
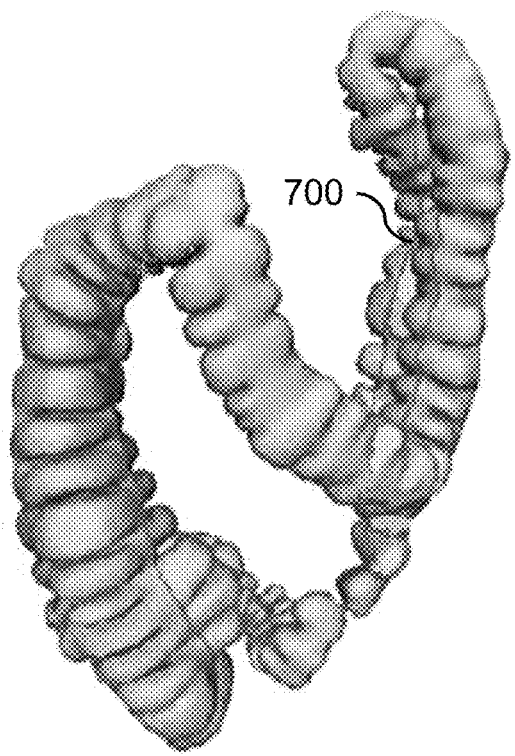
FIG. 7A shows a front view of an exemplary slicing path according to an exemplary embodiment of the present disclosure.
Figure 7B:
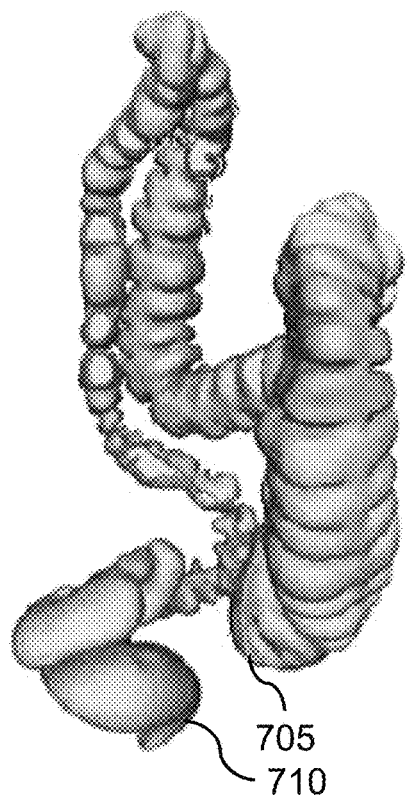
FIG. 7B shows a rear view of an exemplary slicing path according to an exemplary embodiment of the present disclosure.

Given a path 700 along the surface to use for slicing open the tubular structure of FIGS. 7A-B, two small holes (represented by element number 705 and 710) can be punched at each end of the path by removing one face for each. This can yield a structure that is now topologically equivalent to a cylinder (x=0). Slicing along the cutting path is now equivalent to slicing a cylinder from one boundary to another, which can yield a surface with a single boundary (x=I) which is topologically equivalent to the plane. For every vertex along the slicing path, a new vertex can be duplicated with the same position.

As the boundary vertices are mapped to a surface around the 2D skeleton, each boundary vertex can have a correspondence to a position along the skeleton. Two corresponding boundary vertices (i.e., an original vertex from the unsliced mesh and a newly created vertex from the slicing at the same position) are both associated with the same position along the skeleton. The four end vertices on the boundary that result from punching holes at each end can be treated as corner points and are not associated with the skeleton, as they do not contribute to the mapped shape. For all boundary vertices (other than corresponding pairs as mentioned), it is preferable that no two boundaries are associated with the same location along the skeleton.

Since the twists and turns of a structure can often lead to situations where the closest skeletal point for a boundary vertex is actually in a separate section, the location of correspondences between the skeleton and boundary can be created based on finding the nearest boundary point for each skeleton point, determining boundary to skeleton correspondences from the nearest boundary point, and then interpolating positions for boundary points which were not indicated by a skeleton point. The correspondences can be determined for the set of original surface vertices on the slicing path, and then duplicated to the newly created vertices. The first and last vertices along the slicing path can be mapped to the first and last position along the skeleton. An exemplary algorithm for this procedure can be seen below. It should be noted, that the algorithm below is for exemplary purposes only, and an alternate algorithm may be used.

```
for all skeleton points do
    Find nearest boundary vertex
end for
for all vertices on slicing path do
    Find all skeleton points indicated as correspondences
    Take center of those points as true correspondence
end for
for all vertices on slicing path without correspondence do
    Interpolate neighbors
end for
```

Figure 8:
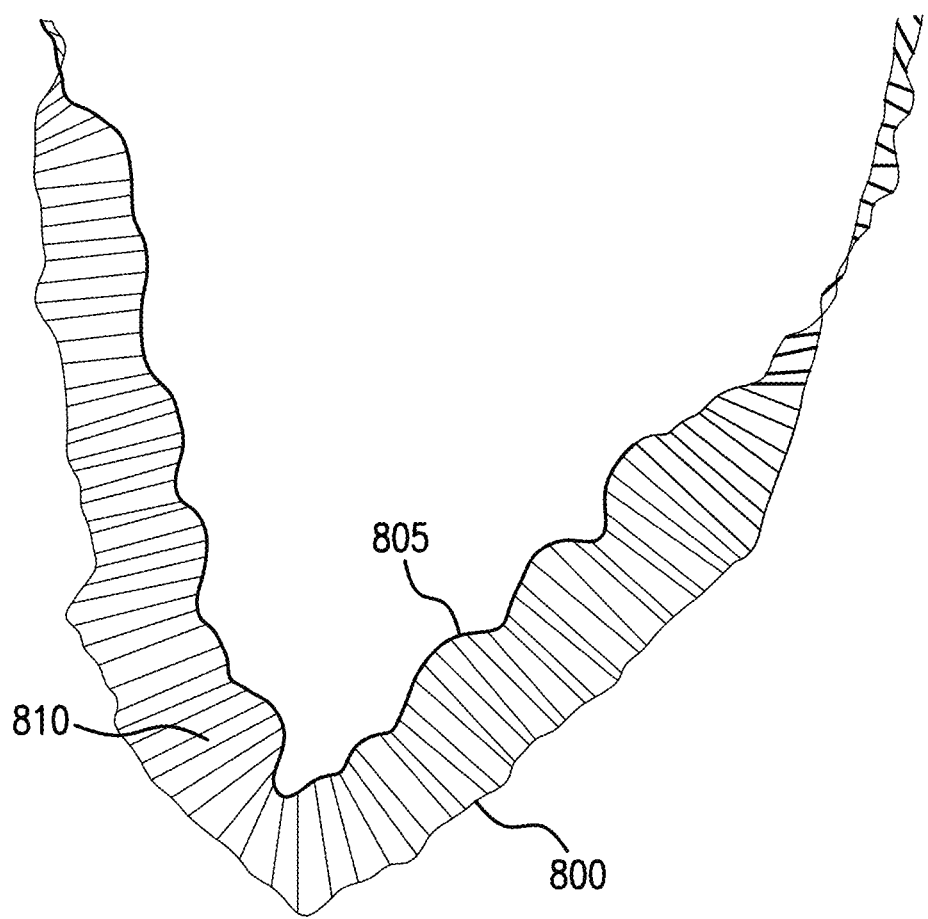
FIG. 8 illustrates a correspondence between boundary vertex points and skeleton points according to an exemplary embodiment of the present disclosure.

The correspondences (excluding the two end points) can then be smoothed through several iterations by setting the current boundary's correspondence position to the average of its two neighbors. The results of this correspondence are shown in FIG. 8 where 800 shows the skeleton path, 805 shows the slicing path, and 810 shows the connections between a boundary point and the skeleton.

The radius for each point along the skeleton can be determined based on the correspondence with the boundary vertices explained above. An exemplary algorithm for this procedure can be seen below. It should be noted, that the algorithm below is for exemplary purposes only, and an alternate algorithm may be used.

```
for all skeleton points s do
    for all boundary vertices v do
        if v corresponds to segment containing s then
            Accumulate weighted distance
            Accumulate weight
        end if
    end for
end for
for all skeleton points do
    if weight is not zero then
        divide distance by weight
    end if
end for
for all skeleton points without radius do
    Interpolate neighbors
end for
```

The radii of the skeleton points can then be iteratively smoothed (again excluding the endpoints) by averaging each skeleton point's radius and its two neighbors.

Figure 9:
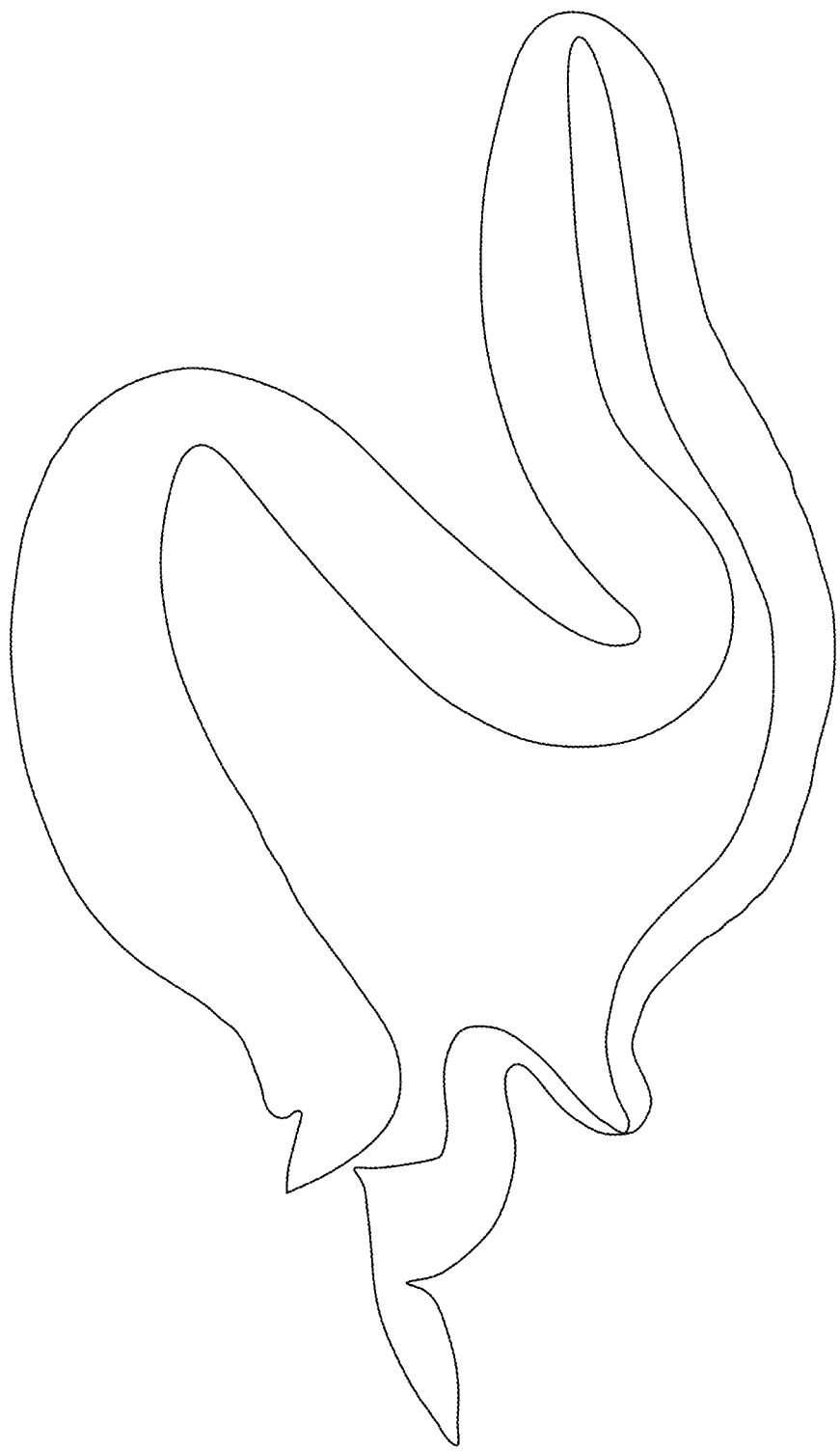
FIG. 9 shows the placement of the boundary in 2D of the tubular structure of FIG. 2A.

The position of the boundary can be determined for every boundary vertex. For every vertex on the slice path (original vertices and newly created vertices), the boundary location on the 2D map for a vertex v can be calculated based on the discrete 2D skeleton points preceding and following the vertex's location on the skeleton. The positions of these before and after points can be $p1=(p1_x, p1_y,)$ and $p2=(p2_x, p2_y,)$, and the radii for the two points can be r1 and r2, respectively. The normalized distance from p1 can be represented by $\alpha$. The new mapped position p for each vertex on the slice path can be calculated using the following exemplary method $$n = p1 - p2, \quad (4)$$

$$d = \begin{bmatrix} d_x \\ d_y \end{bmatrix} = \begin{bmatrix} n_y \\ -n_x \end{bmatrix},$$

$$p0 = p1 * (1 - \alpha) + p2 * \alpha,$$

$$r = r1 * (1 - \alpha) + r2 * \alpha,$$

$$p = \begin{cases} p0 + d * r, & \forall v_i \in M_0 \\ p0 - d * r, & \forall v_i \notin M_0 \end{cases},$$

where $M_0$ can be the original unsliced mesh. The boundary points not on the slice path (from when the holes were punched) can be set to equal intervals between the nearest sliced vertices. A smoothing operation can be applied to remove intersections that might occur, while still preserving the overall general geometric structure. An example of the boundary for the mapping can be seen in FIG. 9.

Given the projected and spaced 2D skeleton of the structure and the boundary placement generated as the target domain $S_2$, the original 3D sliced colon surface $S_1$ can be mapped to the plane. Such mapping preserves the original projected curved information.

Discrete Ricci flow can be used to map the open surface $S_1$ to a rectangle $D_1$ conformally, $\theta_1: S_1 \rightarrow D_1$. Similarly, the target domain $S_2$ can be mapped to another rectangle $D_2$ conformally, $\theta_2: S_2 \rightarrow D_2$. Using harmonic mapping, the one-to-one and onto correspondence $D_1$ and $D_2$ h: $D_1 \rightarrow D_2$ can be computed. Finally, the 2D correspondence can be lifted to the 3D surfaces, f: $S_1 \rightarrow S_2$ and the original 3D surface can be mapped to the designed target domain. The pipeline for the discrete Ricci flow can be represented by the following equation:

$$\begin{array}{ccc} S_1 & \xrightarrow{f} & S_2 \\ \phi_1 \downarrow & & \downarrow \phi_2 \\ D_1 & \xrightarrow{h} & D_2 \end{array} \quad (5)$$

The final result can then be rendered either using mesh rendering with vertex normal information stored from the original structure, or using volume rendering through the original volumetric dataset.

To map the 3D surface to the 2D plane, discrete Ricci flow can be used. Ricci flow is a powerful tool for geometric analysis, and it has been used to successfully prove the Poincaré conjecture. It behaves like heat diffusion, deforming one Riemannian metric to another Riemannian metric conformally, which can be shown in the following equation:

$$\frac{dg}{dt} = -Kdt \quad (6)$$

where g is the Riemannian metric and K is the target curvature.

For the sliced colon surface, the boundary sides between each two corners can be mapped to a straight segment, and the four corners can be mapped to be the right corners of a rectangle. At the same time, the interior surface can be mapped conformally to the plane. Therefore, for discrete Ricci flow, the target curvature of four corners can be set to be $$\frac{\pi}{2}$$

and the curvatures of other boundary vertices and interior vertices can be set to be zero. Similarly, for the generated target domain, the corresponding corner vertices and boundary sides can be computed, the same target curvature can be set, and its conformal rectangular mapping can be obtained. As a mesh can be used for this, the 2D boundary samples can be used as constraints and can perform a constrained Delaunay triangulation to generate the triangular target domain.

Next the one-to-one and onto correspondence can be computed between two rectangles by minimizing the harmonic energy. The resulting harmonic mapping obtains the smoothest deformation between two rectangles. In general, the original 3D colon surface $S_1$ and the 2D target domain $S_2$ are not conformally equivalent. Their conformal modules (the ratios between height and width for the conformal mappings $D_1$ and $D_2$) can be quite different.

From the computation of the target boundary placement, the correspondence of boundary vertices can be known. The positions of the target boundary vertices can then be used as the constrained condition in the harmonic mapping, as shown in the following equations:

$$\text{harmonic energy } E = \sum_{edge(i,j) \in D_2} \|h(v_i) - h(v_j)\|^2 \quad (7)$$

$$\text{harmonic mapping } \Delta h = 0, \; h|_{\partial D_2} = \phi_1(S_1)|_{\partial D_1} \quad (8)$$

where $v_i$ is the ith vertex and (i,j) is the edge of $<v_i, v_j>$ in the discrete triangular mesh $D_2$.

The rectangle $D_2$ of the target curved domain $S_2$ can be mapped to the rectangle $D_1$ of the 3D sliced colon surface $S_1$ to get $D'_2$. Now $D'_2$ and $D_1$ are well aligned. Then, the correspondence h: $D_1 \rightarrow D_2$ can be obtained. Therefore, the correspondence between 3D surfaces can be recovered by $f = \theta_2^{-1} \circ h \circ \theta_1 : S_1 \rightarrow S_2$. The 3D colon surface is now mapped to the target boundary domain, as shown in FIG. 2C The flattened map can then be volume rendered (e.g., using original computed tomography) similarly to how other flattened surfaces have been rendered as known in the art. Given the flattened (u, v) coordinates for each vertex, these can be used to place the map in the 2D plane. Each vertex's original (x, y, z) coordinates can then be used to reference the original location within the volume from which the surface was extracted.

For each vertex, a virtual camera position can also be established. This position can be taken to be the nearest skeleton point in relation to the flattened mesh. Since the boundary points are already associated with a skeleton point, the nearest boundary vertex can be found for each inner vertex. The boundary vertex's corresponding skeleton point can then be taken to be the virtual camera position for that vertex. Using this information, volumetric ray casting can be performed to generate the final images (see FIG. 2C).

The colon data used can generally come from volumes with an approximate size of 512×512×400 voxels. Preprocessing of the volumes can include electronic cleansing, segmentation, triangular mesh extraction, and skeleton extraction, processes which are known in the art. The meshes obtained can be very large (typically over 1.5 million faces) and can be simplified to approximately 5% of their original size. The skeleton can be discretized using various spacing (e.g., a spacing of 1 mm). The exemplary system, method and computer readable medium can be useful in mapping colon surfaces, which are notoriously twisty, to a plane in such a way that preserves the overall context.

In the exemplary method, major bends of the colon can be preserved, and an indication of the colon's radius along the skeleton is also present. In addition to the colon shown in FIG. 2A, a second mapping example is shown in FIGS. 10A-E with the original mesh (FIG. 10A), 2D shaped skeleton (FIG. 10B), and a rendered result (FIG. 10C). Since volume rendering is used to create the final image, even small polyps are easily-observable. The colon shown in FIG. 10C has a small 4 mm polyp near the rectum, which can be seen in the zoomed in version of this region (FIG. 10D), which is closer to the viewing level one would use if scanning the surface for polyps, and the polyp 1000 can be readily observed as a small oval bump on the surface. A further close-up of the polyp 1000 on the flat colon is shown in FIG. 10E.

Figure 11A:
FIG. 11A shows a top section of a straight map adjusted for the radius of the colon of FIG. 2A.
Figure 11B:
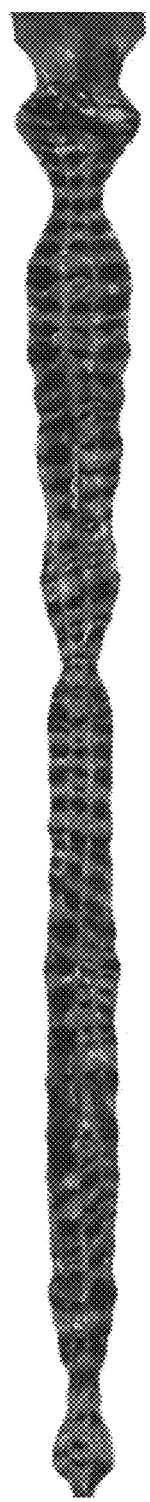
FIG. 11B shows a bottom section of a straight map adjusted for the radius of the colon of FIG. 2A.

Compared with straightened mappings, these exemplary context preserving maps allow for a greater understanding of the general geometry of the structure. The colon in FIG. 2A can be mapped to a straight rectangle, and can also be mapped as a straightened representation accounting for radius in FIGS. 11A-B, which show top and bottom sections of a straight map adjusted for the radius of the colon. Compared to both, the general geometry of the colon is well preserved.

In addition to better preserving the geometric structure, the exemplary maps can also make more intuitive use of a region that is squarer than round. This is readily observable when comparing the context preserving map from FIG. 2C to the straight maps in FIGS. 11A-B. The straightened versions require much greater contiguous space along a single axis if they are to be presented without breaks, while the exemplary context preserving map makes better use of a squarish block of space, such as a defined window on a display.

The exemplary method has the advantage in creating flattened maps of 3D tubular structures which preserve the overall geometric context of the object. The exemplary method is based on first projecting the skeleton of the structure to the optimal 2D plane. This 2D skeleton can then be untangled and adjusted to approximate the geometric shape of the object. A boundary can be placed around the adjusted 2D skeleton to define the boundary of the object that is sliced opened to be mapped. Using this boundary, the 3D sliced surface can be mapped using discrete Ricci flow to a rectangle, and this rectangle can then be deformed using harmonic mapping to match the target boundary. The exemplary method performs the flattening operation such that it creates a context preserving map of the structure. The user can then observe their progression along this map as they navigate inside the structure, without worrying about regions being occluded.

Figure 12:
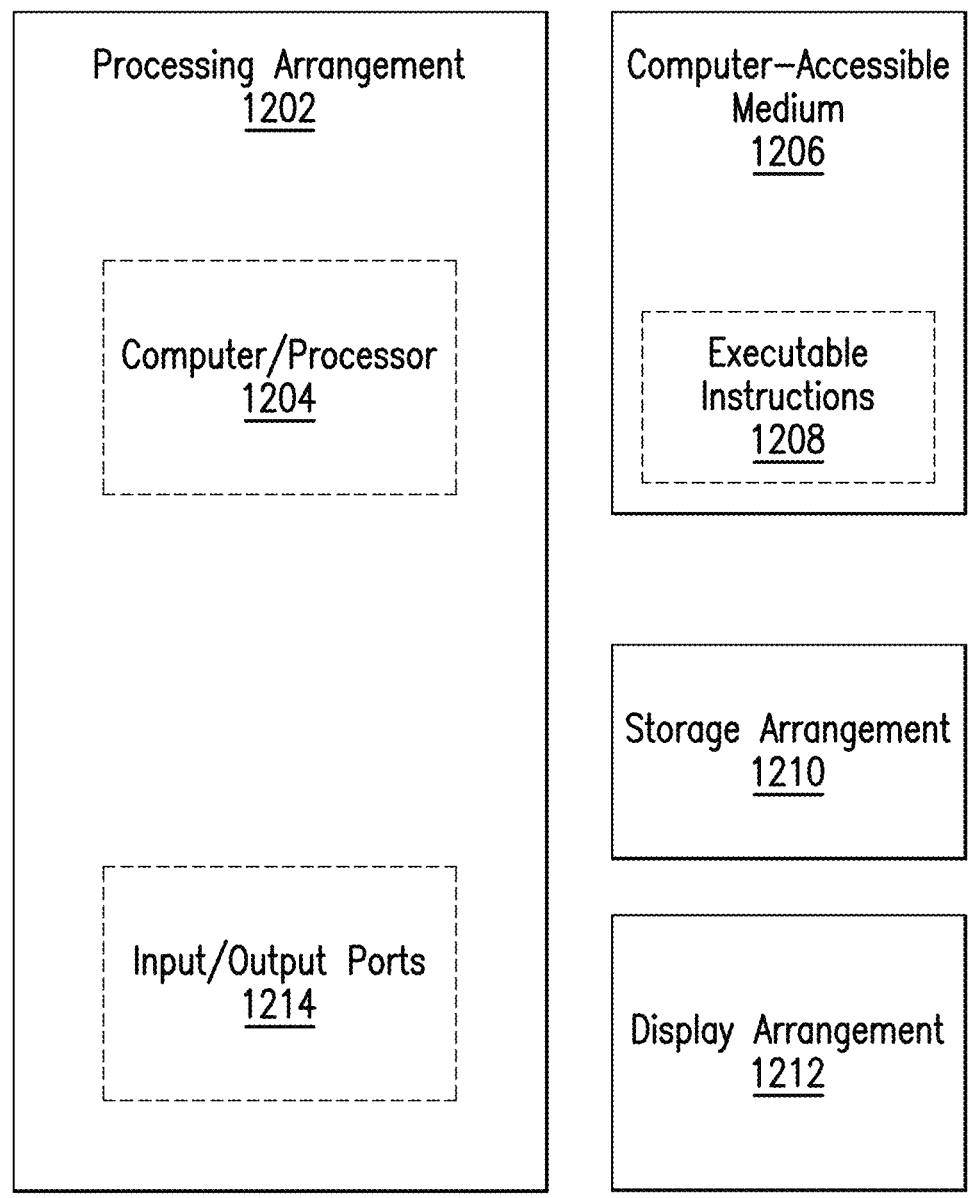
FIG. 12 is an illustration of an exemplary block diagram of an exemplary system in accordance with certain exemplary embodiments of the present disclosure.

FIG. 12 shows a block diagram of an exemplary embodiment of a system suitable for practicing the process described above for generating context preserving maps according to the present disclosure. For example, exemplary procedures in accordance with the present disclosure described herein can be performed by a processing arrangement and/or a computing arrangement 1202. Such processing/computing arrangement 1202 can be, e.g., entirely or a part of, or include, but not limited to, a computer/processor 1204 that can include, e.g., one or more microprocessors, and use instructions stored on a computer-accessible medium (e.g., RAM, ROM, hard drive, or other storage device).

As shown in FIG. 12, e.g., a computer-accessible medium 1206 (e.g., as described herein above, a storage device such as a hard disk, floppy disk, memory stick, CD-ROM, RAM, ROM, etc., or a collection thereof) can be provided (e.g., in communication with the processing arrangement 1202). The computer-accessible medium 1206 can contain executable instructions 1208 thereon. In addition or alternatively, a storage arrangement 1210 can be provided separately from the computer-accessible medium 1206, which can provide the instructions to the processing arrangement 1202 so as to configure the processing arrangement to execute certain exemplary procedures, processes and methods, as described herein above, for example.

Further, the exemplary processing arrangement 1202 can be provided with or include an input/output arrangement 1214, which can include, e.g., a wired network, a wireless network, the internet, an intranet, a data collection probe, a sensor, etc. As shown in FIG. 12, the exemplary processing arrangement 1202 can be in communication with an exemplary display arrangement 1212, which, according to certain exemplary embodiments of the present disclosure, can be a touch-screen configured for inputting information to the processing arrangement in addition to outputting information from the processing arrangement, for example. Further, the exemplary display 1212 and/or a storage arrangement 1210 can be used to display and/or store data in a user-accessible format and/or user-readable format.

Any and all references specifically identified in the specification of the present application are expressly incorporated herein in their entirety by reference thereto. The term "about," as used herein, should generally be understood to refer to both the corresponding number and a range of numbers. Moreover, all numerical ranges herein should be understood to include each whole integer within the range.

While illustrative embodiments of the disclosure are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present disclosure.

What is claimed is:

1. A computer-based method for context preserving mapping of tubular structures represented by a three-dimensional (3D) dataset comprising:

using a computer processor, processing the 3D dataset to project a skeleton of a 3D tubular structure on to a two-dimensional (2D) plane;

using the computer processor, processing the projected skeleton to remove intersections and to untangle the skeleton, wherein the untangling comprises first searching for abutments, then searching for loops, and then searching for crossings;

using the computer processor, determining a 3D boundary for a map of the tubular structure about the skeleton; and using the computer processor, mapping a 3D surface of the skeleton to match the 3D boundary to create a 3D map.

2. The method of claim 1, further comprising further processing to modify the skeleton to separate areas lying close to each other.

3. The method of claim 1, further comprising volumetric ray casting through an original CT data from which a mesh is extracted to generate a more detailed 3D map.

4. The method of claim 1, wherein a surface of a 2D structure of a 2D map is mapped to a surface of a 2D rectangle.

5. The method of claim 4, wherein the 2D map is mapped using Ricci flow.

6. The method of claim 1, wherein determining the boundary comprises slicing open the skeleton from end to end and corresponding each boundary vertex with the skeleton.

7. The method of claim 6, further comprising embedding each boundary vertex into 2D at an associated radius orthogonal to the 2D skeleton.

8. The method of claim 1, wherein the projection of the skeleton is based on a discretized skeleton curve.

9. The method of claim 1, further comprising adjusting the projected skeleton to correct projection imbued distortion in skeleton length prior to processing the skeleton.

10. The method of claim 9, wherein the adjusting the skeleton comprises straightening and lengthening the skeleton.

11. The method of claim 10, wherein lengthening of the skeleton comprises bending a straight skeleton with even spacing into a shape of a projected skeleton.

12. The method of claim 1, wherein the projecting of the skeleton comprises projecting points of an orthogonal projection of a 3D skeleton on a 2D plane.

13. The method of claim 1, further comprising viewing the 3D map on a display.

14. The method of claim 1, wherein the tubular structure is internal to a human body.

15. A system for context preserving mapping of tubular structures represented by a three-dimensional (3D) dataset comprising:

a computer hardware arrangement configured to:

project a skeleton of a 3D tubular structure on to a two-dimensional (2D) plane;

process the skeleton to remove intersections and to untangle the skeleton, wherein the untangling comprises first searching for abutments, then searching for loops, and then searching for crossings;

determine a 3D boundary for a map; and map a 3D surface of the skeleton to match the 3D boundary to create a 3D map.

16. The system of claim 15, wherein the computer hardware arrangement is further configured to adjust the projected skeleton to correct projection imbued distortion in the skeleton prior to processing the skeleton.

17. A non-transitory computer readable media having instructions encoded thereon readable by a computer processor for performing generating context preserving mapping of tubular structures represented by a three-dimensional (3D) dataset, the instructions comprising:
   instructions for a computer processor to process the 3D dataset to project a skeleton of a 3D tubular structure on to a two-dimensional (2D) plane;
   instructions for the computer processor to process the projected skeleton to remove intersections and to untangle the skeleton, wherein the untangling comprises first searching for abutments, then searching for loops, and then searching for crossings;
   instructions for the computer processor to determine a 3D boundary for a map of the tubular structure about the skeleton; and
   instructions for the computer processor to map a 3D surface of the skeleton to match the 3D boundary to create a 3D map.

18. A computer-based method for context preserving mapping of tubular structures represented by a three-dimensional (3D) dataset comprising:
   using a computer processor, processing the 3D dataset to project a skeleton of a 3D tubular structure on to a two-dimensional (2D) plane;
   using the computer processor, adjusting the projected skeleton to correct projection imbued distortion in skeleton length by straightening and lengthening the skeleton, wherein the lengthening of the skeleton comprises bending a straight skeleton with even spacing into a shape of a projected skeleton;
   using the computer processor, processing the projected skeleton to remove intersections;
   using the computer processor, determining a 3D boundary for a map of the tubular structure about the skeleton; and
   using the computer processor, mapping a 3D surface of the skeleton to match the 3D boundary to create a 3D map.

19. The method of claim 18, further comprising further processing to modify the skeleton to separate areas lying close to each other.

20. The method of claim 18, further comprising volumetric ray casting through an original CT data from which a mesh is extracted to generate a more detailed 3D map.

21. The method of claim 18, wherein a surface of a 2D structure of a 2D map is mapped to a surface of a 2D rectangle.

22. The method of claim 21, wherein the 2D map is mapped using Ricci flow.

23. The method of claim 18, wherein determining the 3D boundary comprises slicing open the skeleton from end to end and corresponding each boundary vertex with the skeleton.

24. The method of claim 23, further comprising embedding each boundary vertex into 2D at an associated radius orthogonal to the 2D skeleton.

25. The method of claim 18, wherein the projection of the skeleton is based on a discretized skeleton curve.

26. The method of claim 18, wherein the projecting of the skeleton comprises projecting points of an orthogonal projection of a 3D skeleton on a 2D plane.

27. The method of claim 18, further comprising viewing the 3D map on a display.

28. The method of claim 18, wherein the tubular structure is internal to a human body.

29. The method of claim 18, wherein the processing comprises untangling the skeleton.

30. The method of claim 29, wherein the untangling of the skeleton comprises searching the skeleton for at least one of abutments, loops or crossings.

31. The method of claim 30, wherein a priority for searching the skeleton comprises first searching for abutments, then searching for loops, and then searching for crossings.

32. A system for context preserving mapping of tubular structures represented by a three-dimensional (3D) dataset comprising:
   a computer hardware arrangement configured to:
      project a skeleton of a 3D tubular structure on to a two-dimensional (2D) plane;
      adjust the projected skeleton to correct projection imbued distortion in skeleton length by straightening and lengthening the skeleton, wherein the lengthening of the skeleton comprises bending a straight skeleton with even spacing into a shape of a projected skeleton;
      process the skeleton to remove intersections;
      determine a 3D boundary for a map; and
      map a 3D surface of the skeleton to match the 3D boundary to create a 3D map.

33. A non-transitory computer readable media having instructions encoded thereon readable by a computer processor for performing generating context preserving mapping of tubular structures represented by a three-dimensional (3D) dataset, the instructions comprising:
   instructions for a computer processor to process the 3D dataset to project a skeleton of a 3D tubular structure on to a two-dimensional (2D) plane;
   instructions for the computer processor to adjust the projected skeleton to correct projection imbued distortion in skeleton length by straightening and lengthening the skeleton, wherein the lengthening of the skeleton comprises bending a straight skeleton with even spacing into a shape of a projected skeleton;
   instructions for the computer processor to process the projected skeleton to remove intersections;
   instructions for the computer processor to determine a 3D boundary for a map of the tubular structure about the skeleton; and
   instructions for the computer processor to map a 3D surface of the skeleton to match the 3D boundary to create a 3D map.

* * * * *

UNITED STATES PATENT AND TRADEMARK OFFICE
CERTIFICATE OF CORRECTION

PATENT NO. : 9,792,729 B2
APPLICATION NO. : 14/353168
DATED : October 17, 2017
INVENTOR(S) : Arie Kaufman et al.

It is certified that error appears in the above-identified patent and that said Letters Patent is hereby corrected as shown below:

In the Specification

Please amend the first paragraph under Column 1, Lines 18-22 with the following paragraph as follows:

STATEMENT OF GOVERNMENT RIGHTS
This invention was made with government support under EB007530 awarded by the National Institutes of Health and CCF0702699, IIS0916235, CNS0959979 awarded by the National Science Foundation. The government has certain rights in the invention.

Signed and Sealed this
First Day of January, 2019

Andrei Iancu
*Director of the United States Patent and Trademark Office*